United States Patent [19]
Hashimoto et al.

[11] Patent Number: 5,681,297
[45] Date of Patent: Oct. 28, 1997

[54] DEVICE FOR DISPOSING EXCREMENT

[75] Inventors: Takeo Hashimoto; Kimio Sato, both of Tokyo, Japan

[73] Assignee: Niles Parts Co., Ltd., Japan

[21] Appl. No.: 636,523

[22] Filed: Apr. 23, 1996

[30] Foreign Application Priority Data

May 30, 1995 [JP] Japan .................. 7-155407

[51] Int. Cl.$^6$ .................. A61F 5/44
[52] U.S. Cl. .................. 604/355; 604/393; 4/616; 119/164
[58] Field of Search .................. 604/327, 347, 604/355, 393; 4/455, 457, 480, 484, 616; 119/164; 273/318

[56] References Cited

U.S. PATENT DOCUMENTS

| | | | |
|---|---|---|---|
| 3,626,941 | 12/1971 | Webb | 604/347 |
| 4,517,953 | 5/1985 | Osaka et al. | 273/318 |
| 5,342,583 | 8/1994 | Son | 604/393 |

FOREIGN PATENT DOCUMENTS

4-364841  12/1992  Japan .

*Primary Examiner*—Robert A. Clarke
*Attorney, Agent, or Firm*—Ronald P. Kananen

[57] ABSTRACT

A device for disposing excrement, comprising a diaper cup (1) having a main body (101) for encompassing a human body's hip and buttocks, a washing water sending hose (105) connected to the main body (101) for passing washing water to an interior of the diaper cup (1), and a human waste sucking hose (104) connected to the main body (101) for sucking washing water and waste from the interior of the diaper cup (1). A front cover (103) is mounted to the main body (101) of the diaper cup (1) through bellows joints (102) so that the front cover (103) can be freely bent. A sensor coupler (107) is electrically connected to a bowel movement perceiving sensor (109) mounted to the main body (101) of the diaper cup (1). The washing water sending hose (105), human waste sucking hose (104), and sensor coupler (107) are bundled together into a single hose unit (123) to facilitate attachment and removal of the hoses and sensor coupler from the main body (101) of the diaper cup (1). A plurality of nozzles (108a, 108b) are disposed within the main body (101) of the diaper cup (1) for ejecting washing water to key spots of a human body's hip and buttocks. A light sensor is provided for disabling the device upon removal from the user.

9 Claims, 10 Drawing Sheets

DEVICE FOR DISPOSING EXCREMENT

BACKGROUND OF THE INVENTION

1. Field of the Invention

This invention relates generally to excrement disposing devices for sick, aged, and other bedridden patients who are not able to use conventional restroom facilities. In particular, the present invention relates to excrement disposing devices that automatically dispose human waste and clean dirty spots due to excrement, especially in cases when bedridden people produce excrement while lying in bed.

2. Description of the Related Art

Excrement disposing devices are known in the prior art, such as, for example, the device disclosed in Japanese Patent Publication No. HEI 4-364841 (1992). This conventional device has a structure that encompasses the hip and buttocks of a human body with a diaper cup made out of soft insulating materials, washes excrement produced inside the diaper cup, and eliminates the waste out of the diaper cup with the use of a pump. To this diaper cup various types of hoses and cords are attached, such as a hose that passes washing water, a human waste sucking hose, and a sensor cord that detects excretion inside the diaper cup.

This conventional excrement disposing device has a number of disadvantages. For example, washing water and excrement tends to leak out through the periphery of the diaper cup as a result of the poor adhesiveness of the device to the hip and buttocks. This poor adhesiveness results from the difficulty in fitting the device to various body shapes due to a limit in flexibility, even when soft insulating materials are employed.

Also, with the conventional disposing device, there exists a rubbing problem that occurs in the crotch area due to the diaper cup.

Another shortcoming with the conventional disposing device is that there exists a difficulty in handling that results from the requirement that each hose and each cord must be put on and taken off separately.

Furthermore, since there is only one nozzle that ejects washing water to the inside of the diaper cup, problems such as poor washing persist. Also, when maintenance work is conducted by removing the diaper cup from the human body, washing water may be ejected by mistake, or the washing system may engage when the excrement perception sensor picks up a detection mistakenly.

SUMMARY OF THE INVENTION

An object of the present invention is to solve the problems associated with the conventional excrement disposing device described above. More specifically, it is an object of the present invention to provide an excrement disposing device that is easy to fit to various body shapes, that allows each hose and each cord to be put on and taken off as a single unit, that provides an improved washing effect, and that provides fail safe operations during maintenance of the device.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

In accordance with the present invention, in order to solve the problems described above, the present invention provides an excrement disposing device comprising a diaper cup having a main body that encompasses a human body's hip and buttocks, a hose connected to the main body of the diaper cup that passes washing water to an interior of the diaper cup, and a human waste sucking hose connected to the main body of the diaper cup that sucks the washing water and the waste from the interior of the diaper cup. The main body of the diaper cup is equipped with a front cover mounted to the main body through bellows joints so that the front cover can be freely bent.

A section between the bellows joints is preferably covered with waterproof cloth. The main body of the diaper cup is preferably equipped with snap hooks that enables diapers to be easily installed and exchanged.

In a further aspect of the present invention, in accordance with its objects and purposes, the apparatus hereof may also comprise an excrement disposing device comprising a diaper cup having a main body that encompasses a human body's hip and buttocks, a hose connected to the main body of the diaper cup that passes washing water to an interior of the diaper cup, a human waste sucking hose connected to the main body of the diaper cup that sucks the washing water and the waste from the interior of the diaper cup, and a sensor coupler that is electrically connected to a bowel movement perceiving sensor installed at the main body of the diaper cup. The washing water sending hose, the human waste sucking hose, and the sensor coupler, are bundled together into a single hose unit to facilitate attachment and removal from the main body of the diaper cup. The hose unit is preferably equipped with a holding piece that enables the hose unit to be fixed to the main body of the diaper cup. The main body of the diaper cup is preferably equipped with a front cover mounted to the main body through bellows joints so that the front cover can be freely bent. The main body of the diaper cup is preferably equipped with a plurality of nozzles that can eject washing water to key spots of a user's hip and buttocks. The ejecting range of the washing water from the nozzles can be respectively varied according to which areas are to be washed. The bowel movement perceiving sensor preferably includes a light sensor for detecting removal of the diaper from the user.

BRIEF DESCRIPTION OF THE DRAWINGS

The present invention will become more clearly appreciated as a disclosure of the preferred embodiments is made with reference to the accompanying drawings. In the drawings:

FIG. 3 illustrates a hip board used in conjunction with the first embodiment of the present invention.

DETAILED DESCRIPTION OF THE PREFERRED EMBODIMENTS

A first embodiment of the present invention will now be described in detail with reference to FIGS. 1 to 9.

Figure 8:
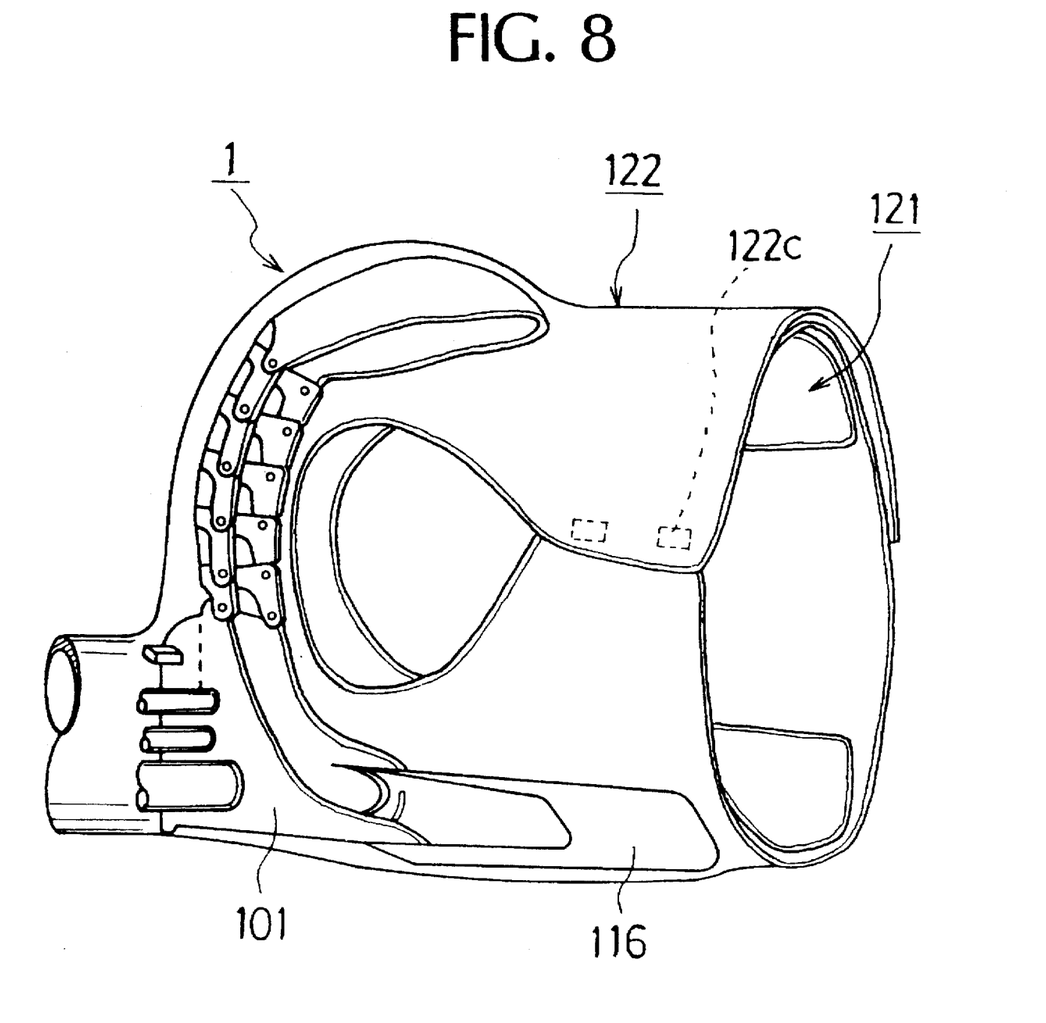
FIG. 8 is a perspective view of the same components shown in FIG. 7 in a fully assembled condition.

As shown in FIG. 8, a diaper cup 1 according to the present invention has a main body 101, a hip board 116, an exchangeable diaper 121, and a diaper cover 122. These components of the invention will be explained in order.

First, referring to FIG. 1, an explanation will be given of the main body 101 of the diaper cup 1.

Figure 1:
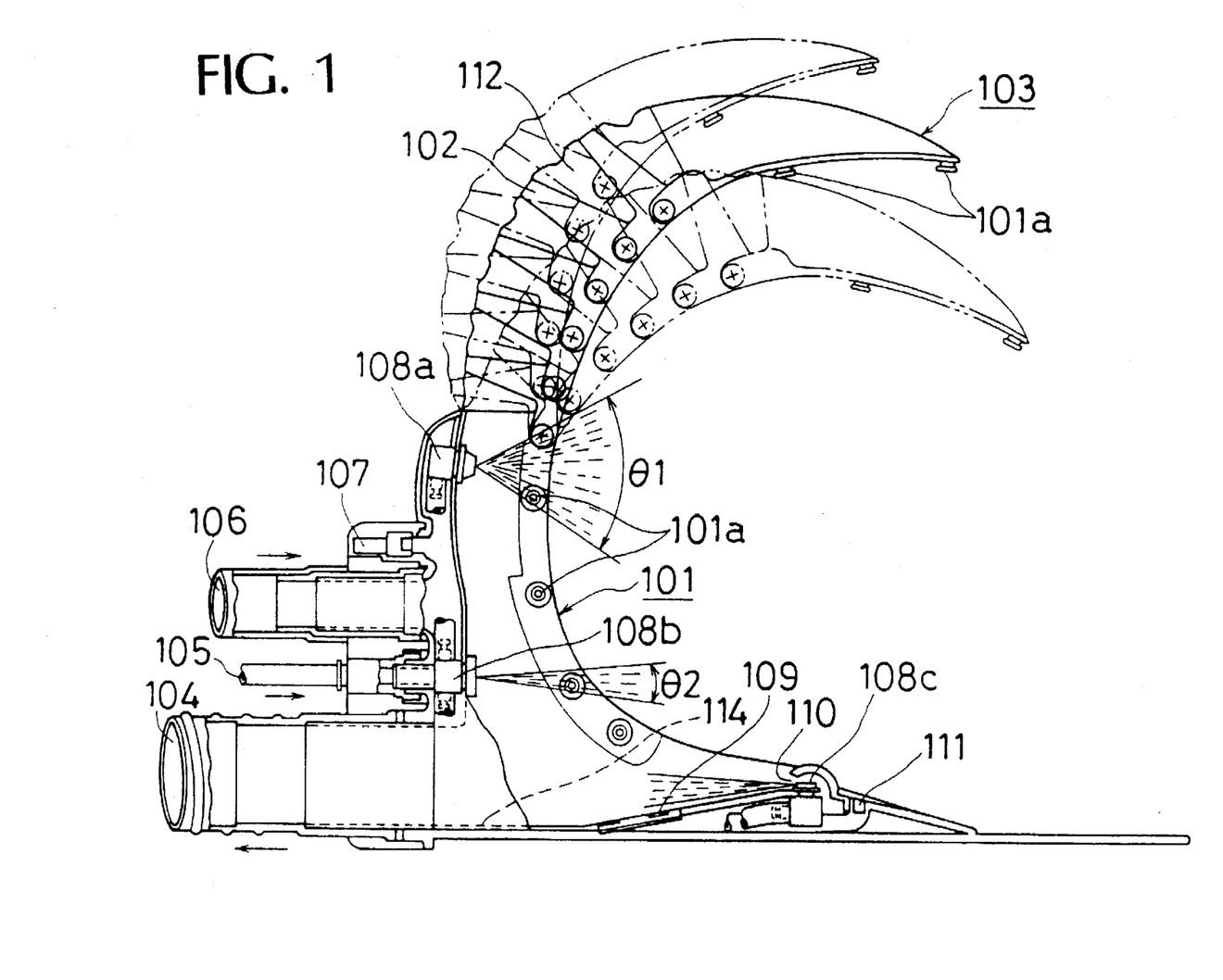
FIG. 1 is a side view that shows the main body of a diaper cup according to a first embodiment of the present invention.

FIG. 1 shows the main body 101 of the diaper cup 1, which is designed to encompass the human body's hip and buttocks. The main body 101 of the diaper cup 1 is equipped with a front cover 103 for covering a front pubic region. The front cover 103 is built for free bending by employing bellows joints 102. The bellows joints 102 comprise a series of laterally disposed link members extending between the main body 101 and the front cover 103. The link members are pivotally connected to each other on their right and left sides. A rear one of the link members is pivotally connected to the main body 101, and a front one of the link members is pivotally connected to the front cover 103. The link members allow the front cover 103 to be easily and comfortably positioned over the front of the user when the diaper cover 122 is secured in position about the user's hip and buttocks. The bellows joints 102 are covered with waterproof cloth 112, which prevents leakage of washing water while permitting the bending function of the bellows joints 102.

The main body of the diaper cup 1 is equipped with snapping hooks 101a, a nozzle 108a for washing the pubic region, a nozzle 108b for washing the anus, a nozzle 108c for washing the cup 1, a bowel movement perceiving sensor 109, an outlet 110 for blowing warm air, an auxiliary sucking hole 111, and a urine perceiving sensor 114.

The snapping hooks 101a on the diaper cup 1 permit the exchangeable diapers 121 (FIG. 5) to be put on and taken off of the diaper cup 1. A plurality of the snapping hooks 101a are lined up in series on the diaper cup 1 so as to correspond with the snapping hooks 121b on the diapers 121.

The nozzle 108a for washing the pubic region and the nozzle 108b for washing the anus are specifically designed for separately washing the pubic region and the anus, respectively, of the patients who wear the diaper cup 1. The ejecting range Θ1 of the nozzle 108a for washing the pubic region is designed to be a wider angle than the ejecting range Θ2 of the nozzle 108b for washing the anus.

The nozzle 108c for washing the cup 1 functions to wash away the excrement produced by the patients who wear the diaper cup 1. The nozzle 108c is installed near the warm air outlet 110, and both are open toward the bowel movement perceiving sensor 109. The bowel movement perceiving sensor 109 and the urine perceiving sensor 114 function to detect the excrement produced by the patient. Both of the sensors 109 and 114 are installed near the nozzle 108c for washing the cup.

The bowel movement perceiving sensor 109 is composed of a proximity or contact sensor and a light sensor. The proximity or contact sensor detects the presence of excrement. The light sensor functions to halt the operation of the system and prevent a mistaken operation when the main body 101 of the diaper cup 1 is removed from the user's body, thereby exposing the light sensor to light. The light sensor can be, for example, a photoresistor made of cadmium sulfide (CdS).

The auxiliary sucking hole 111 is designed for sucking the washing water, and so forth, that flows to the upper side of the body. The auxiliary sucking hole 111 is located near the nozzle 108c on the opposite side of the nozzle 108c from the bowel movement perceiving sensor 109.

Figure 2:
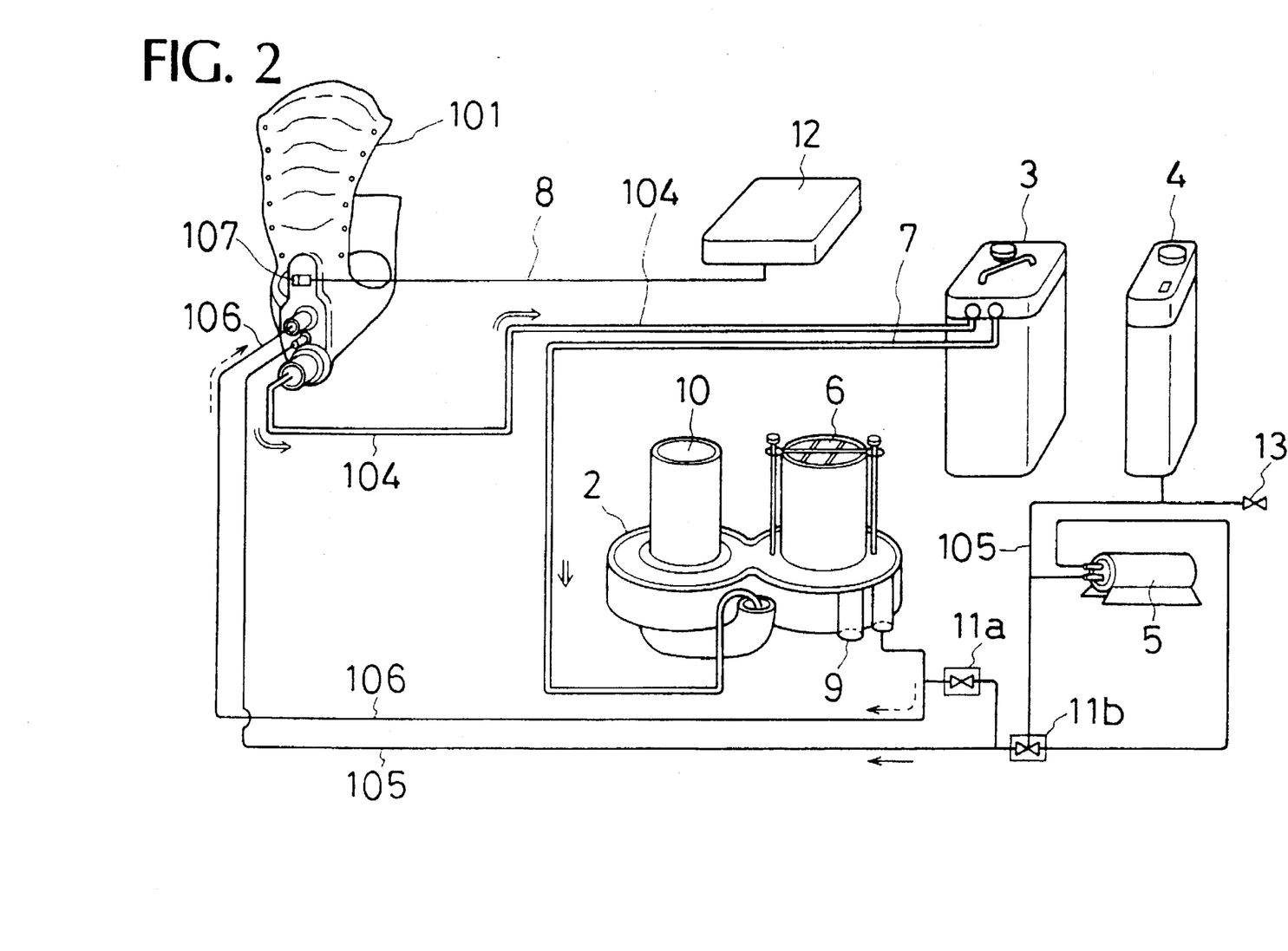
FIG. 2 is a block diagram that shows the main body of the diaper cup connected to external facilities.
Figure 3A:
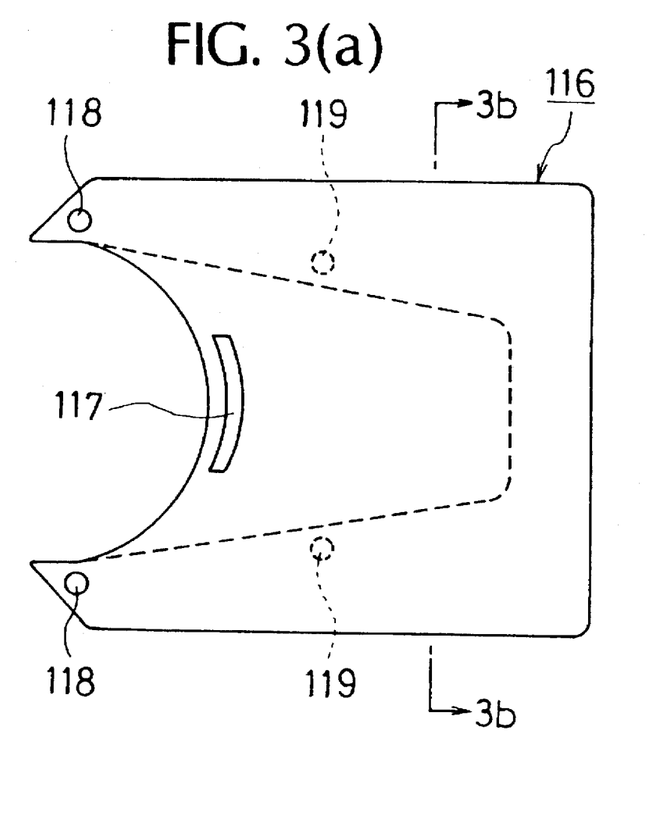
FIG. 3(a) is a plan view of the hip board.
Figure 3B:
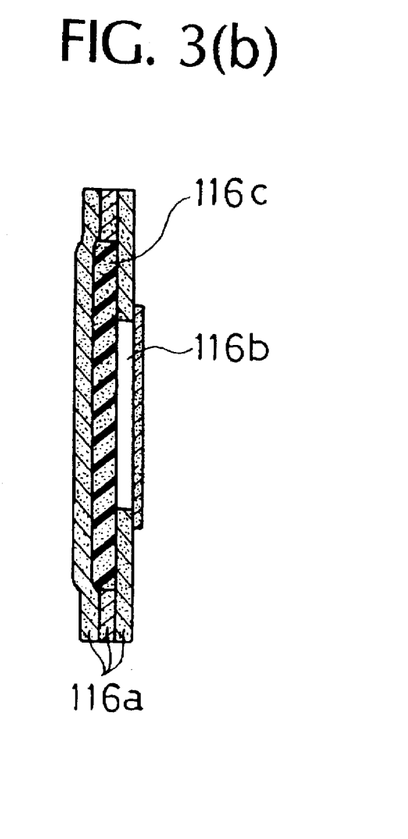
FIG. 3(b) is a cross-sectional view along line A—A in FIG. 3(a).

The main body 101 of the diaper cup 1 is connected to external facilities, as shown in FIG. 2, through a human waste sucking hose 104 that sucks the washing water and waste from the interior of the main body 101 of the diaper cup 1, a washing water sending hose 105 that passes washing water to the interior of the main body 101 of the diaper cup 1, a warm air sending hose 106 that sends warm air to the interior of the main body 101 of the diaper cup 1, and a sensor coupler 107 that derives the electric signals from the bowel movement perceiving sensor 109 and the urine perceiving sensor 114.

The human waste sucking hose 104 is connected to a vacuum motor housing 2 via an excrement tank 3 and a vacuum hose 7. The washing water sending hose 105 is connected to a warm water tank 4 via an ejection adjustment valve 11b for the washing water and a water sending pump 5. The warm air sending hose 106 is connected to the vacuum motor housing 2. The sensor coupler 107 is connected to a sequencer 12 via a sensor signal line 8. The vacuum motor housing 2 is equipped with a filter box 6, an exhaust pipe 9, and a suction pipe 10 for cooling the motor (not shown). The human waste sucking hose 104 and the washing water sending hose 105 are connected by the water removing valve 11a. A water draining valve 13 is connected to the warm water tank 4.

Figure 4:
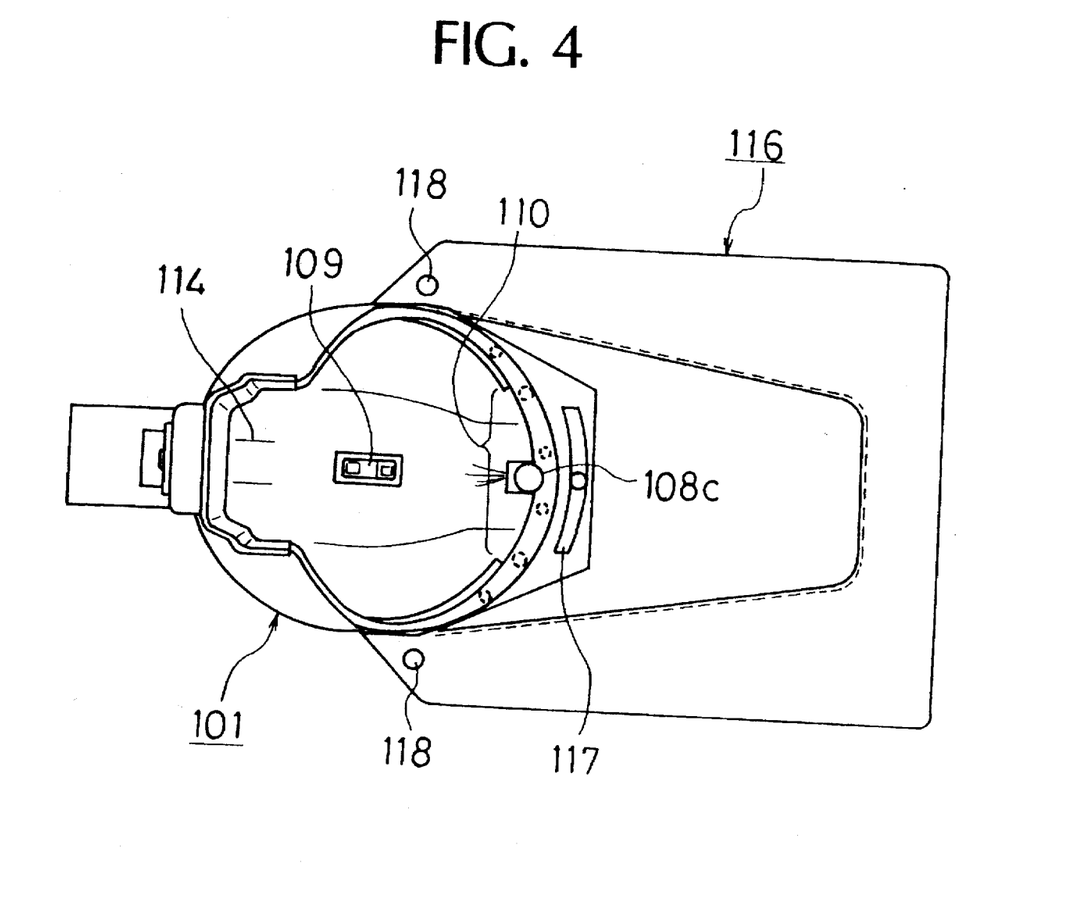
FIG. 4 is a plan view of the combined main body of the diaper cup shown in FIG. 1 and the hip board shown in FIG. 3.

Next, referring to FIGS. 3 and 4, an explanation will be given of the hip board 116.

The hip board 116 is designed to make maintenance easier and to enable free handling when putting the hip board 116 on and taking it off from the main body 101 of the diaper cup 1. As shown in FIG. 3, the hip board 116 is equipped with a 3-layer structured urethane padding 116a. An insertion space 116b is provided for receiving the main body 101 of the cup 1. A cushion 116c is enclosed within the urethane padding 116a.

A long hole 117 is formed on the hip board in a position corresponding with the auxiliary suction hole 111 installed on the main body 101 of the cup 1. A button 118 is provided for releasably fastening the hip board 116 to an exchangeable diaper 121. Snapping hooks 119 are provided for fixing the hip board 116 to the main body of the cup 1. FIG. 4 shows the condition in which the hip board 116 is attached to the main body 101 of the cup 1.

Figure 5:
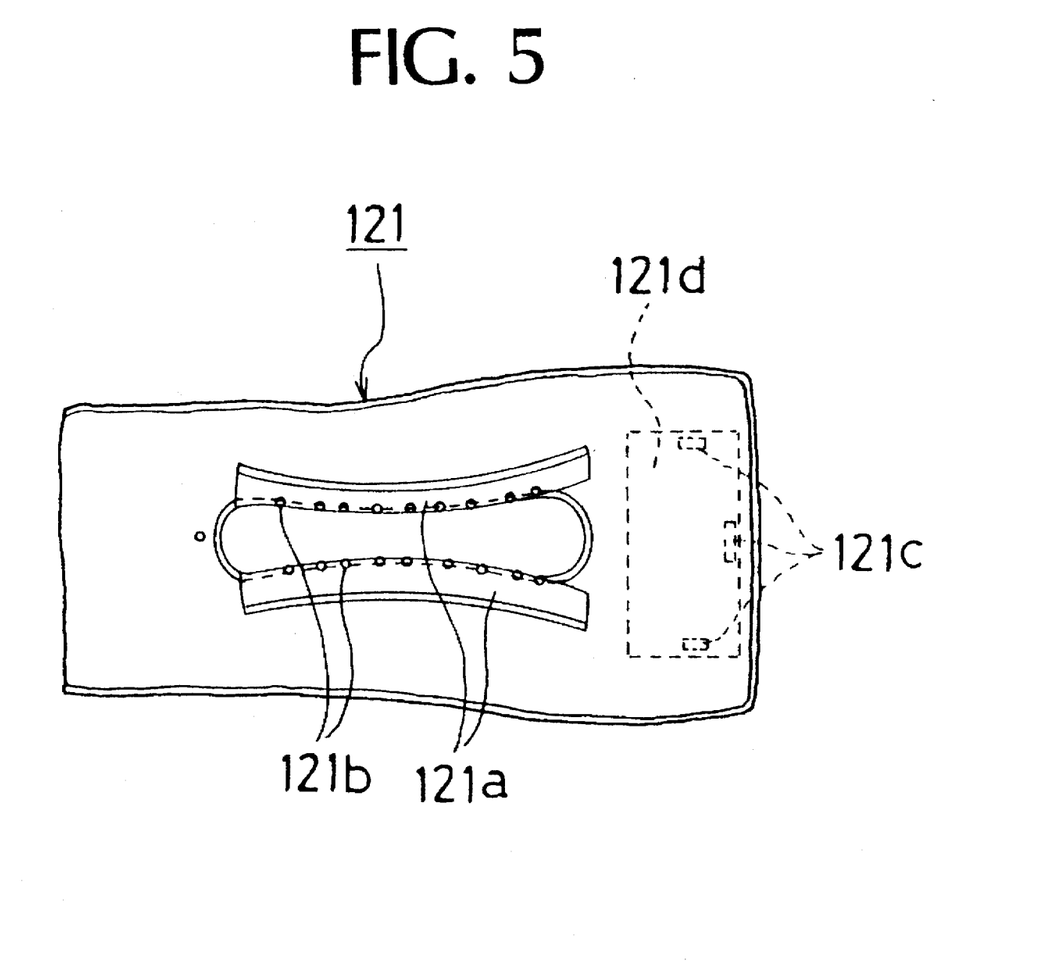
FIG. 5 is a plan view of an exchangeable diaper used in conjunction with the first embodiment of the present invention.

Next, referring to FIG. 5, an explanation of the exchangeable diapers 121 will be provided.

As shown in FIG. 5, the exchangeable diaper is equipped with frill 121a for preventing leakage around the sides, snapping hooks 121b on the diaper's side that are positioned to correspond to the snapping hooks 101a on the cup's side, fastener strips 121c (e.g., hook and pile fastener strips or adhesive tape strips) that are positioned to correspond to the fastener strips 122a on the diaper cover 122, and a bag 121d into which the hip board 116 is inserted.

Figure 6:
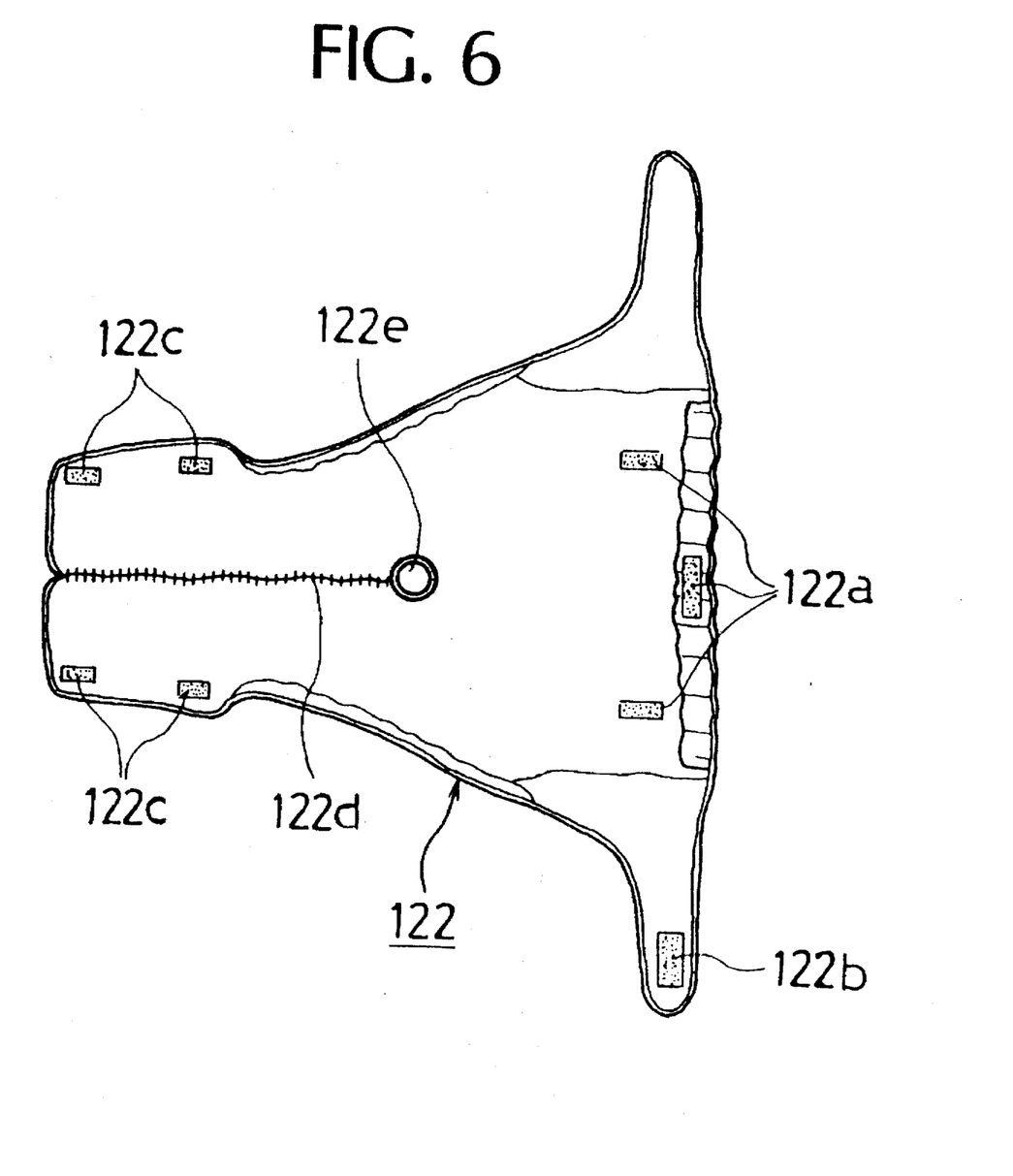
FIG. 6 is a plan view of a diaper cover used in conjunction with the first embodiment of the present invention.

Next, referring to FIG. 6, an explanation of the diaper cover 122 will be provided.

As shown in FIG. 6, the diaper cover 122 is equipped with fastener strips 122a, 122b and 122c, a zipper 122d, and a passing through hole 122e for a hose unit. The diaper cover 122 and the exchangeable diaper 121 are secured to each other by the respective fastener strips 122a and 121c. The diaper cover 122 is fixed to the human body by fastener strips 122b and 122c being stuck together in the manner of a conventional diaper. The zipper 122d is installed in such a way that the diaper cover alone can be removed by opening the zipper 122d even while the hose unit 123 remains connected to the main body 101 of the diaper cup 1.

Figure 7:
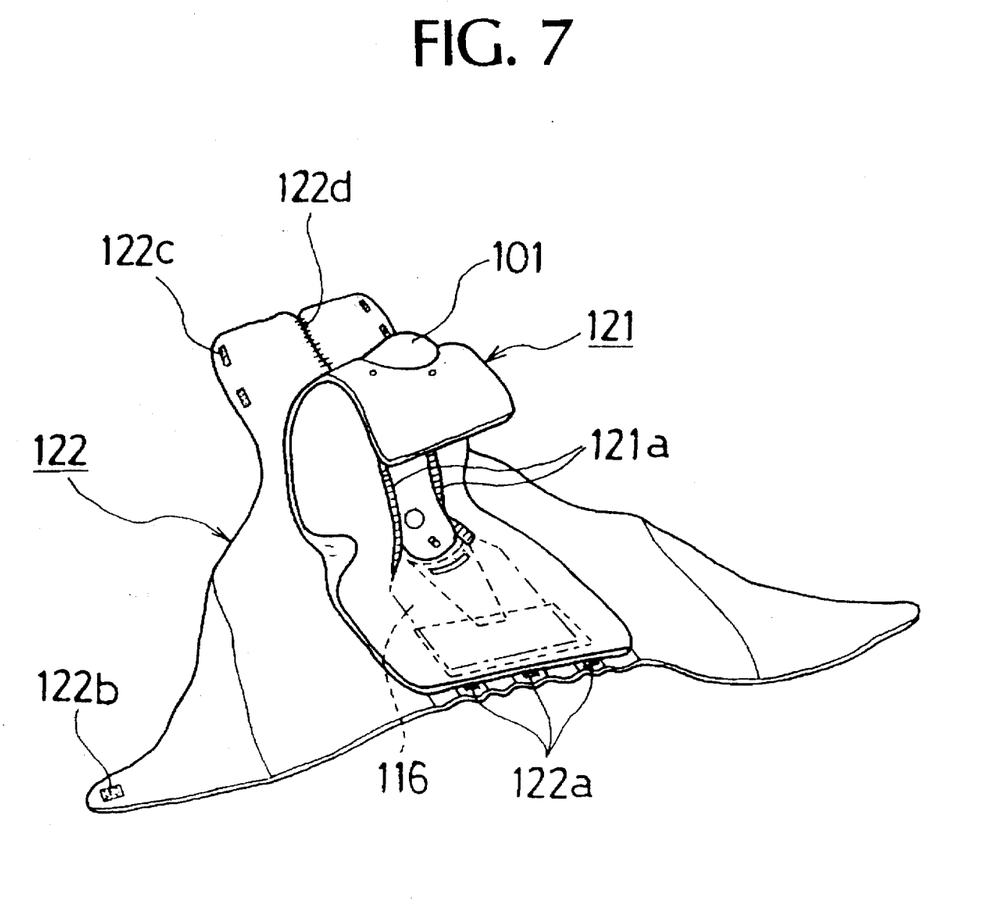
FIG. 7 is a perspective view showing a partially assembled condition of the main body of the diaper cup, the hip board, the exchangeable diaper, and the diaper cover according to the first embodiment of the present invention.

The main body 101 of the diaper cup 1, the hip board 116, the exchangeable diaper 121, and the diaper cover 122 are assembled in the following manner. As shown in FIG. 7, the hip board 116 is first installed on the main body 101 of the diaper cup 1. The exchangeable diaper 121 and the main body 101 of the diaper cup 1 are then fastened together with the snapping hooks 121b and the snapping hooks 101a, and the hip board 116 is inserted into the bag 121d of the exchangeable diaper 121. The exchangeable diaper 121 and the diaper cover 122 are then fastened together with the fastener strips 121c and 122a. In this way, the assembled diaper cup 1, as shown in the FIG. 8, is completed.

Figure 9:
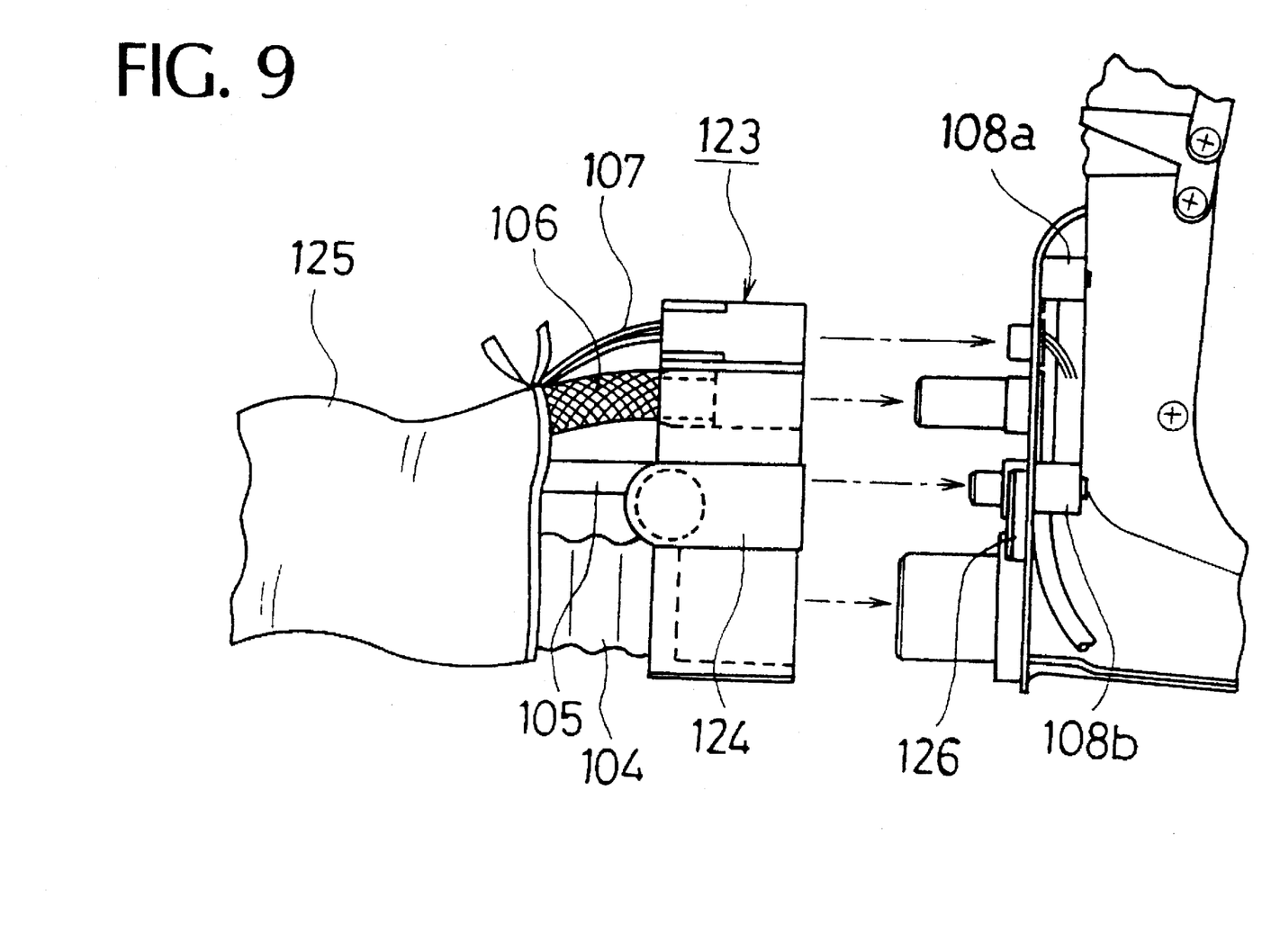
FIG. 9 is a side view of a hose unit used in conjunction with the first embodiment of the present invention.

As shown in FIG. 9, the assembled diaper cup 1 is connected to the hose unit 123. The hose unit 123 provides a connection between the diaper cup 1 and the external facilities. The hose unit 123 bundles the human waste sucking hose 104, the washing water sending hose 105, the warm air sending hose 106, and the sensor coupler 107 together. The hose unit 123 can therefore be attached and removed from the main body 101 of the diaper cup 1 as a single unit. A holding piece 124 is fixed to the clasp 126 on the side of the main body 101 of the diaper cup 1. A hose cover 125 preferably covers the bundle of hoses connected to the hose unit 123.

Figure 10:
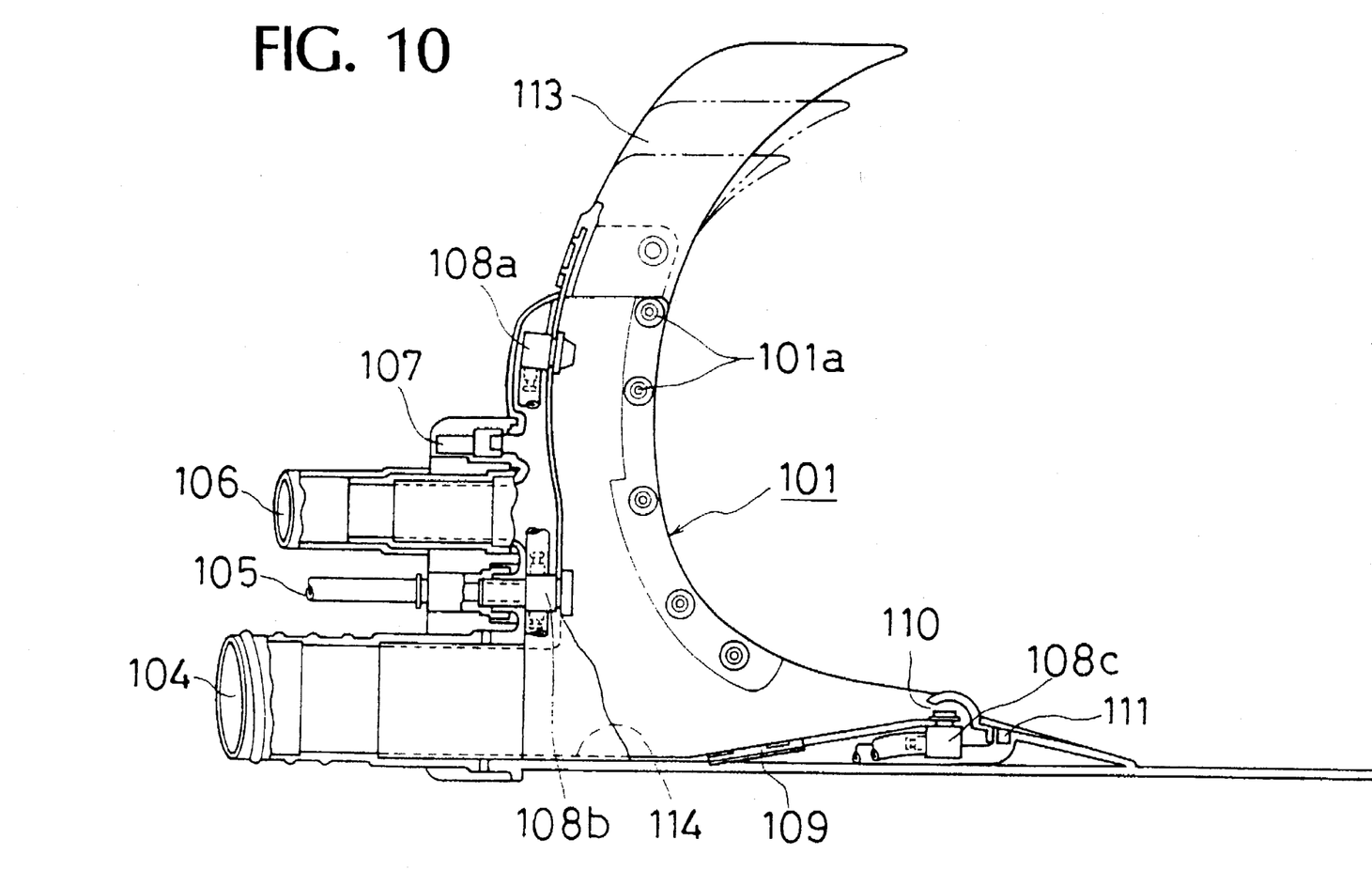
FIG. 10 is a side view of the main body of a diaper cup according to a second embodiment of the present invention.

FIG. 10 shows a second embodiment of the present invention. The second embodiment is basically the same as the first embodiment, except that the front cover 103 used in the first embodiment is replaced with a supporter 113 for feminine use. The supporter 113 can be made in a variety of different sizes, for instance large, middle and small sizes, according to the sizes of the intended users' bodies. The supporter 113 is connected to the main body 101 of the diaper cup 1.

The excrement disposing devices of the present invention provide the following advantages as a result of the structures and functions described above.

Since the main body of the diaper cup is equipped with a front cover that is built in such a way that it can be freely bent by employing the bellows joints, it is much easier to fit the diaper cup to various types of bodies, and the rubbing problems in the crotch area due to the diaper cup will not occur.

Also, this invention brings about ease in setting up and taking off every type of hose and cord from the diaper cup, since the washing water sending hose, the human waste sucking hose, and the sensor coupler are held together as a single unit by the hose unit, and the hose unit is designed to be freely attached and removed from the main body of the diaper cup.

Furthermore, the main body of the diaper cup is equipped with more than one nozzle that can eject washing water to each key spot of the patient's hip and buttocks, and the ejecting range of the washing water from the nozzles is respectively varied according to the condition and location of each key spot. This arrangement of nozzles provides improved washing results.

Since the light sensor installed with the bowel movement perceiving sensor is set up in such a way that it will halt the operation of the system when the light sensor detects a certain light, washing water is not ejected by mistake when conducting maintenance work requiring removal of the diaper cup from the human body.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

We claim:

1. A device for disposing excrement, comprising:

a diaper cup having a main body for encompassing a human body's hip and buttocks;

a washing water sending hose connected to the main body of the diaper cup for passing washing water to an interior of the diaper cup; and a human waste sucking hose connected to the main body of the diaper cup for sucking washing water and waste from the interior of the diaper cup;

wherein the main body of the diaper cup is equipped with a front cover that can be freely bent; and wherein the front cover is mounted to the main body of the diaper cup through bellows joints, and said bellows joints permit said front cover to be freely bent.

2. The device for disposing excrement according to claim 1, further comprising a waterproof cloth covering the bellows joints.

3. A device for disposing excrement, comprising:

a diaper cup having a main body for encompassing a human body's hip and buttocks;

a washing water sending hose connected to the main body of the diaper cup for passing washing water to an interior of the diaper cup; and a human waste sucking hose connected to the main body of the diaper cup for sucking washing water and waste from the interior of the diaper cup;

wherein the main body of the diaper cup is equipped with a front cover that can be freely bent; and further comprising snap hooks mounted to the main body of the diaper cup for enabling diapers to be removably attached to the main body.

4. A device for disposing excrement, comprising:

a diaper cup having a main body that encompasses a human body's cup and buttocks;

a washing water sending hose connected to the main body of the diaper cup for passing washing water to an interior of the diaper cup;

a human waste sucking hose connected to the main body of the diaper cup for sucking washing water and waste from the interior of the diaper cup; and a sensor coupler electrically connected to a bowel movement perceiving sensor mounted to the main body of the diaper cup;

wherein said washing water sending hose, human waste sucking hose, and sensor coupler are bundled together into a single hose unit to facilitate attachment and removal from the main body of the diaper cup;

further comprising a plurality of nozzles disposed within the main body of the diaper cup for ejecting washing water to key spots of a human body's hip and buttocks;

wherein an ejecting range of washing water from said plurality of nozzles is respectively varied according to areas to be washed by the nozzle.

5. A device for disposing excrement, comprising:

a diaper cup having a main body that encompasses a human body's hip and buttocks;

a washing water sending hose connected to the main body of the diaper cup for passing washing water to an interior of the diaper cup;

a human waste sucking hose connected to the main body of the diaper cup for sucking washing water and waste from the interior of the diaper cup; and a sensor coupler electrically connected to a bowel movement perceiving sensor mounted to the main body of the diaper cup;

wherein said washing water sending hose, human waste sucking hose, and sensor coupler are bundled together into a single hose unit to facilitate attachment and removal from the main body of the diaper cup; and wherein said bowel movement perceiving sensor includes a light sensor for detecting removal of the diaper from the user.

6. A device for disposing excrement, comprising:

a diaper cup having a main body that encompasses a user's hip and buttocks;

a washing water sending hose connected to the main body of the diaper cup for passing washing water to an interior of the diaper cup; and a human waste sucking hose connected to the main body of the diaper cup for sucking washing water and waste from the interior of the diaper cup;

wherein a front cover is mounted to the main body of the diaper cup for covering a front pubic region of the user, said front cover being flexibly mounted to the main body through a series of pivotal link members connected between the main body and the front cover.

7. The device for disposing excrement according to claim 6, wherein said washing water sending hose and said human waste sucking hose are bundled together into a single hose unit to facilitate attachment and removal of the hoses from the main body of the diaper cup.

8. The device for disposing excrement according to claim 7, further comprising a sensor coupler electrically connected to a sensor within the main body for detecting bowel movement, and a warm air hose for supplying warm air to the diaper cup, said sensor coupler and said warm air hose being bundled into said single hose unit along with said washing water sending hose and said human waste sucking hose.

9. A device for disposing excrement, comprising:

a diaper cup having a main body that encompasses a human body's hip and buttocks;

a washing water sending hose connected to the main body of the diaper cup for passing washing water to an interior of the diaper cup;

a human waste sucking hose connected to the main body of the diaper cup for sucking washing water and waste from the interior of the diaper cup; and a sensor coupler electrically connected to a bowel movement perceiving sensor mounted to the main body of the diaper cup;

wherein said washing water sending hose, human waste sucking hose, and sensor coupler are bundled together into a single hose unit to facilitate attachment and removal from the main body of the diaper cup; and further comprising a front cover mounted to the main body of the diaper cup through bellows joints, and said bellows joints permit said front cover to be freely bent.

* * * * *